United States Patent [19]
Roussis et al.

[11] Patent Number: 5,905,195
[45] Date of Patent: May 18, 1999

[54] METHOD FOR ANALYZING TOTAL REACTIVE SULFUR

[75] Inventors: Stilianos G. Roussis, Brights Grove; James W. Fedora, Sarnia; Andrew S. Cameron, Edmonton, all of Canada

[73] Assignee: Exxon Research and Engineering Co., Florham Park, N.J.

[21] Appl. No.: 09/076,539

[22] Filed: May 12, 1998

[51] Int. Cl.[6] .......................... G01M 11/00; G01D 18/00; G06F 17/00; G01N 1/00

[52] U.S. Cl. .................................. 73/53.01; 250/252.1 R; 364/498; 73/61.58

[58] Field of Search ................................ 73/53.01, 61.52, 73/61.58, 64.54; 250/281, 252.1 R, 288, 282; 364/498, 413, 554

Primary Examiner—Michael Brock
Assistant Examiner—Jay L. Politzer
Attorney, Agent, or Firm—J. H. Takemoto

[57] ABSTRACT

The invention relates to a method for determining total reactive sulfur in a crude oil or fraction thereof using a mass spectrometer or gas chromatograph and mass spectrometer. Selecting fragment ions characteristic of reactive sulfur species enables the quantitative determination of total reactive sulfur species. The use of a low resolution mass spectrometer allows the rapid determination of total reactive sulfur in field or remote locations where more sophisticated instruments are not available.

5 Claims, 10 Drawing Sheets

METHOD FOR ANALYZING TOTAL REACTIVE SULFUR

FIELD OF THE INVENTION

This invention relates to a method for analyzing for total reactive sulfur in crude oils or fractions thereof using mass spectrometric techniques.

DESCRIPTION OF THE RELATED ART

There has been increasing interest in the determination of total reactive sulfur (TRS) in crude oils due to the declining supplies of sweet crudes and the increasing need to process sour crudes. The prediction of crude corrosivity is important to the economics of crude purchasing and processing. It is known that certain sulfur-containing species or total reactive sulfur are mainly responsible for the corrosivity attributed to sulfur compounds present in crude oils. The total reactive sulfur includes contributions from the following sulfur-containing types: (i) hydrogen sulfide, (ii) mercaptans, (iii) aliphatic sulfides, (iv) aliphatic disulfides, (v) elemental sulfur and (vi) polysulfides.

A combination of wet chemical methods are conventionally required for the determination of total reactive sulfur. The aliphatic sulfides are determined by UV measurement of a sulfur-iodine complex. Mercaptans and hydrogen sulfide are measured by non-aqueous potentiometric titration. Disulfides are measured by conversion to mercaptans using acidic reduction. Polysulfides and elemental sulfur are determined by polaragraphic methods. The main concern of these chemical methods is the determination of aliphatic sulfides which are believed to account for the majority (about 80% or more) of total reactive sulfur species in crudes and fractions thereof. Since aliphatic sulfides contribute at least about 80% or more of the total corrosivity, any problems which affect their measurement affects the final TRS and hence final corrosion values.

The method for determining aliphatic sulfides was originally developed for the 450° F. fraction, and is based on the selective complexation of the "basic" sulfide sulfur atom with iodine. The complex shows a strong band at 308 nm in the UV region. However, this technique suffers from the disadvantage that iodine complexation can also occur with basic nitrogen-containing species which can affect the accuracy of the UV method of analysis.

A more rigorous spectroscopic approach is disclosed by George and Gorbaty, J. Am. Chem. Soc., 111, 3182 (1989) which is based on the sulfur K-Edge X-ray absorption near edge structure spectroscopy and X-ray photoelectron spectroscopy. These techniques have been successfully employed for elucidating organically bound sulfidic sulfur and thiophenic sulfur. Unfortunately, the cost of the requisite equipment is very high thus rendering the technique unavailable for routine analytical purposes.

It is known to use 70 eV electron ionization and chemical ionization mass spectrometric techniques for the identification and quantitation of aromatic sulfur compounds. However, these methods have not been extended to the direct analysis of alkyl sulfides and disulfides which are the species most directly linked to sulfur corrosivity.

It would be desirable to be able to rapidly and inexpensively determine TRS in a crude oil or fraction thereof.

SUMMARY OF THE INVENTION

This invention relates to a method for determining total reactive sulfur in a crude oil or fraction thereof which comprises the steps of:

(1) introducing the crude oil or fraction thereof into a mass spectrometer;

(2) obtaining a series of mass spectra;

(3) selecting fragment ions which are characteristic of reactive sulfur species including hydrogen sulfide, mercaptans, hydrocarbyl sulfides, hydrocarbyl disulfides, elemental sulfur and polysulfides, said fragment ions being selected from at least one of the group consisting of $SH^+$, $CSH^+$; $CH_3S^+$, $C_2H_5S^+$, $H_2S_2^+$ and $S_2^+$:

(4) identifying peaks in the mass chromatograms which are characteristic of at least one of the fragment ions; and (5) quantifying the reactive sulfur species identified by their corresponding fragment ions, wherein the total reactive sulfur is the sum of individual reactive sulfur species.

In another embodiment, this invention relates to a method for determining total reactive sulfur as a function of boiling point for a crude oil or fraction thereof which comprises the steps of:

(1) introducing the crude oil or fraction thereof into a chromatographic separation means which is interfaced to a mass spectrometer thereby causing at least a partial separation of the crude oil or fraction thereof into constituent chemical components as a function of retention time;

(2) introducing the constituent chemical components into a mass spectrometer;

(3) obtaining a series of time resolved mass spectra;

(4) selecting fragment ions which are characteristic of reactive sulfur species including hydrogen sulfides, mercaptans, hydrocarbyl sulfides, hydrocarbyl disulfides, elemental sulfur and polysulfides, said fragment ions being selected from at least one of the group consisting of $SH^+$, $CHS^+$, $CH_3S^+$, $C_2H_5S^+$, $H_2S_2^+$, and $S_2^+$;

(5) identifying peaks in the mass chromatogram which are characteristic of at least one of the fragment ions; and (6) quantifying the reactive sulfur species identified by their corresponding fragment ions as a function of retention time, wherein the total reactive sulfur is the sum of the individual reactive sulfur species.

Yet another embodiment of the invention is directed to a method for determining total reactive sulfur in a crude oil or fraction thereof which comprises the steps of:

(1) introducing the crude oil of fraction thereof into a low resolution mass spectrometer;

(2) obtaining a series of mass spectra;

(3) selecting fragment ions which are characteristic of reactive sulfur species including hydrogen sulfide, mercaptans, hydrocarbyl sulfides, hydrocarbyl disulfides, elemental sulfur and polysulfides, said fragment ions being selected from at least one of the group consisting of $SH^+$, $CSH^+$, $CH_3S^+$, $C_2H_5S^+$, $H_2S_2^+$ and $S_2^+$:

(4) identifying peaks in the mass chromatograms which are characteristic of the nominal masses of at least one of the fragment ions;

(5) selecting reference samples having known values of total reactive sulfur and subjecting said references samples to steps (1) to (4) above;

(6) calibrating the peaks in the mass chromatograms of the reference samples which are characteristic of the nominal masses of the at least one fragment ions against the known values of total reactive sulfur species in the reference samples; and (7) quantifying the reactive sulfur species identified by the nominal masses of their corresponding fragment ions by comparison with the calibration obtained from the reference samples, wherein the total reactive sulfur is the sum of the individual reactive sulfur species.

DETAILED DESCRIPTION OF THE INVENTION

Crude oils and fractions thereof typically contain many different kinds of sulfur-containing species. These species are broadly characterized as being sulfur incorporated into an aromatic ring structure vs. non-aromatic sulfur. Aromatic sulfur compounds such as thiophene and the like are generally not as corrosive when compared to non-aromatic sulfur-containing compounds such as mercaptans (RSH), hydrocarbyl sulfides (RSR) and hydrocarbyl disulfides (RSSR) wherein R is a hydrocarbyl radical. By hydrocarbyl is meant aliphatic, alicyclic, aromatic, aliphatic- and alicyclic-substituted aromatic, and aromatic-substituted aliphatic and alicyclic wherein the hydrocarbyl radicals may be substituted by halogen, nitro, cyano, carboxyl, amino and the like. The nature of hydrocarbyl radical is not critical. Total reactive sulfur is then the sum of the non-aromatic sulfur-containing species including the mercaptans, sulfides and disulfides identified above plus hydrogen sulfide, elemental sulfur and polysulfides ($S_x$).

In the mass spectrometer, sample molecules are bombarded with high energy electrons thereby creating molecular ions which fragment in a pattern characteristic of the molecular species involved. A continuous series of mass spectra are obtained over a scan range of about 10 to 800 Daltons. The mass spectral data may also be acquired in selected ion monitoring mode. In this mode, care must be taken to select ions representative of the components of interest and to operate under repeatable conditions. A variety of mass spectrometers may be used including low resolution, high resolution, MS/MS, ion cyclotron resonance and time of flight. Any ionization technique may be used such as electron ionization, chemical ionization, multiphotonionization, field desoprtion, field ionization and the like, provided that the technique provides either molecular or fragment ions which are suitable for use in the present method.

An important aspect of the present invention is the discovery that certain fragment ions can be used as quantitative indicators of their parent sulfur-containing species. These fragment ions and corresponding sulfur species or compounds are set forth in the following table:

| Fragment ion | mass/charge | Parent sulfur-containing species |
| --- | --- | --- |
| $C_2H_5S^+$ | 61.0112 | RSR/RSH |
| $H_2S_2^+$ | 65.9528 | RSSR |
| $S_2^+$ | 63.9441 | $S_x$, RSSR |
| $CH_3S^+$ | 46.9955 | RSR/RSH/RSSR |
| $CSH^+$ | 44.9799 | RSR/RSH/RSSR, thiophenes |
| $SH^+$ | 32.9799 | $H_2S$, RSR |

Figure 1:
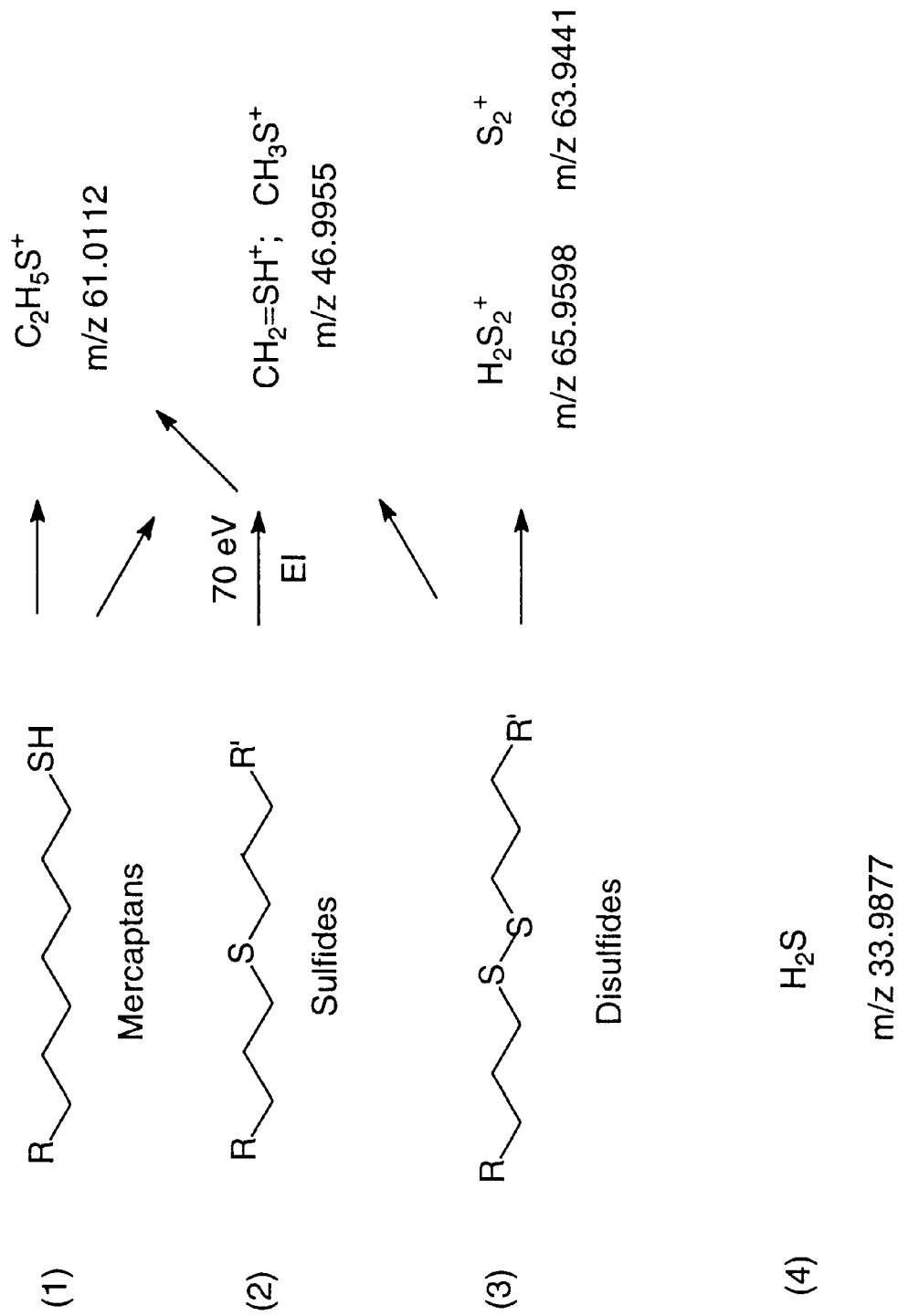
FIG. 1 is a schematic showing reactions of parent molecular species which result in characteristic fragment ions.

The reactions schemes which produce the fragment ions in the mass spectrometer are also illustrated in FIG. 1. By monitoring the masses corresponding to these fragment ions, it is possible to quantitatively ascertain the concentration of TRS species in a given sample. Other fragment ions may substituted if they are quantitative indicators of parent sulfur-containing species.

Figure 2:
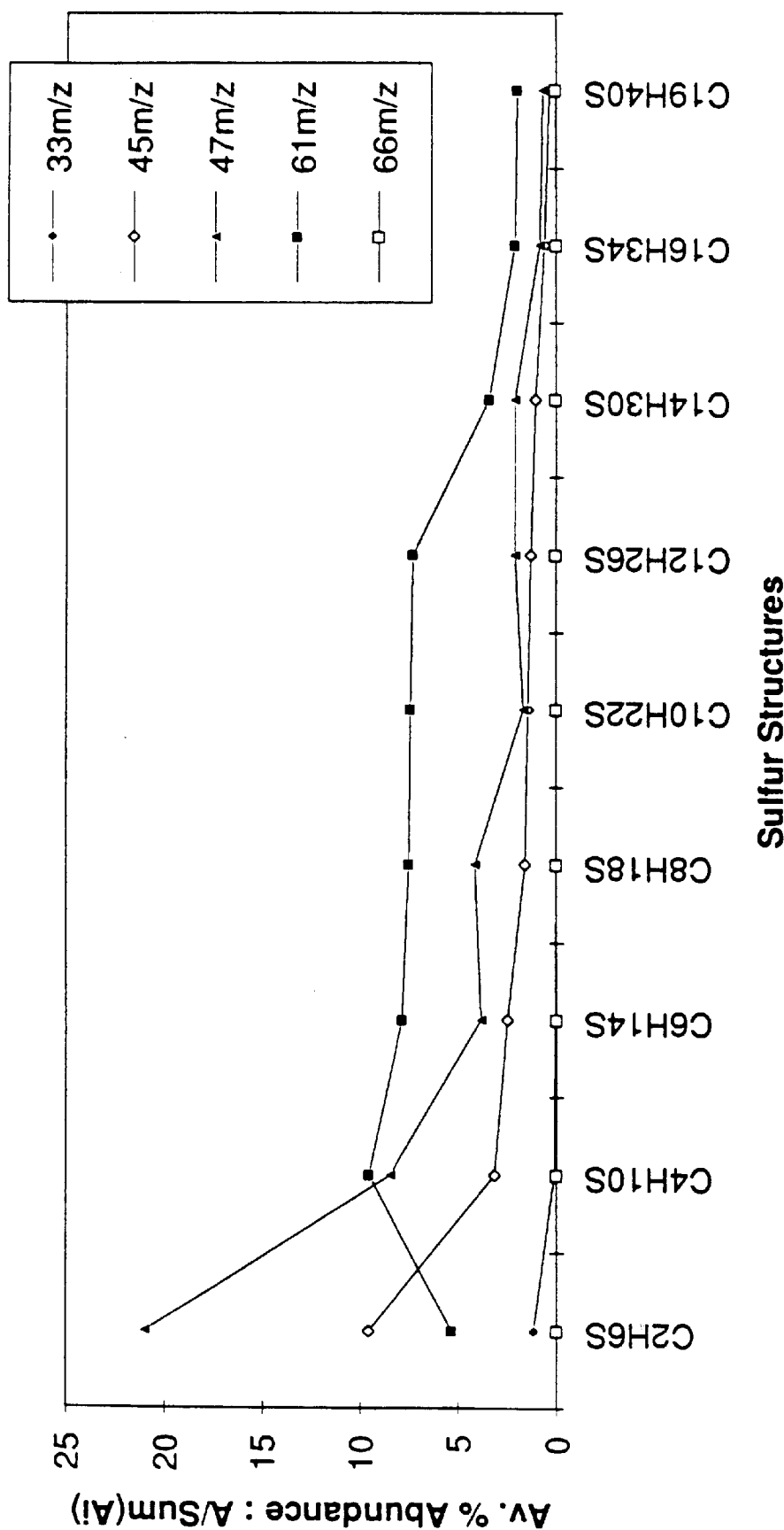
FIG. 2 is a graph showing the relative abundances of selected mass ions in the mass spectra of RSR and RSH compounds.
Figure 3:
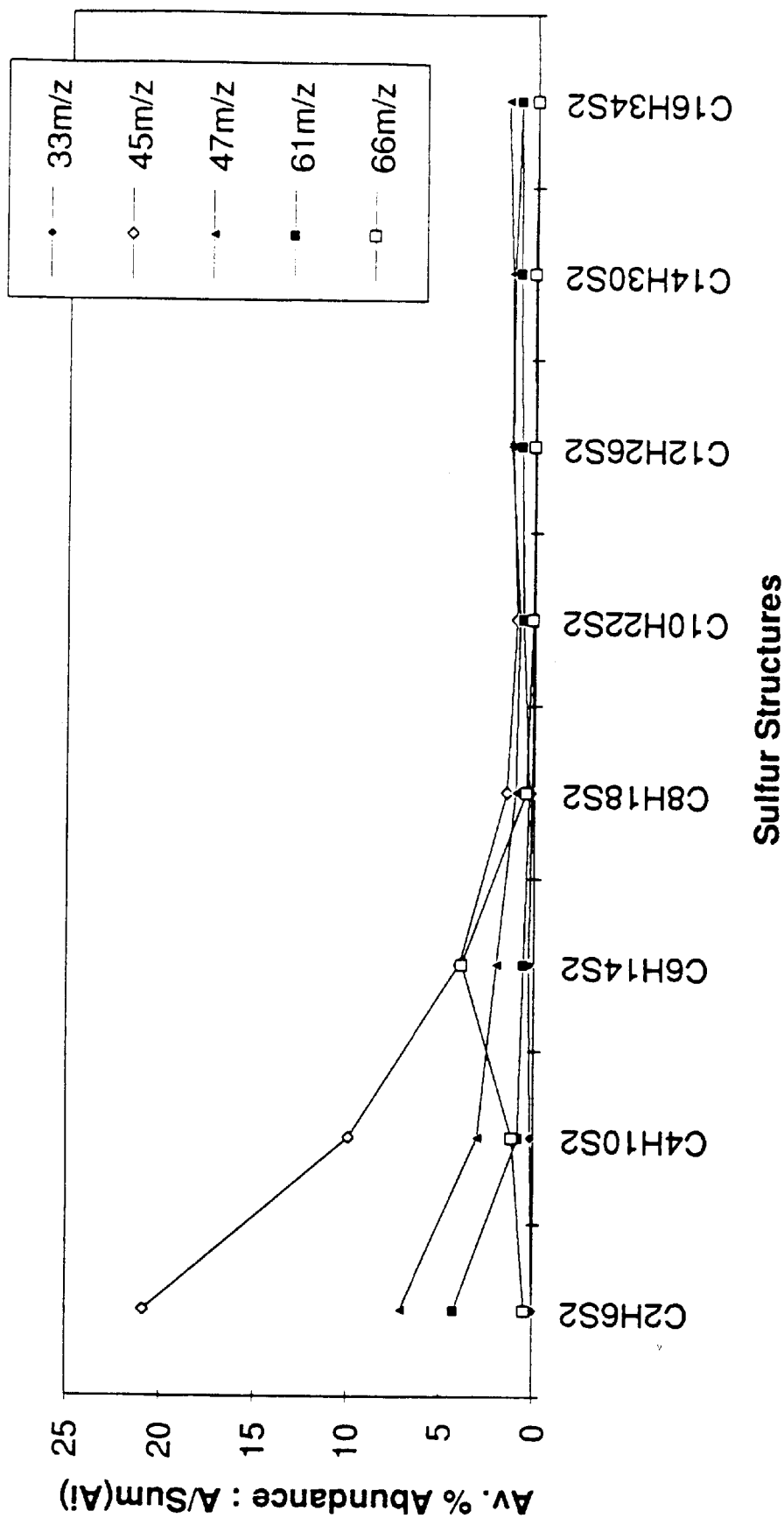
FIG. 3 is a graph showing the relative abundances of selected mass ions in the mass spectra of RSSR compounds.
Figure 4:
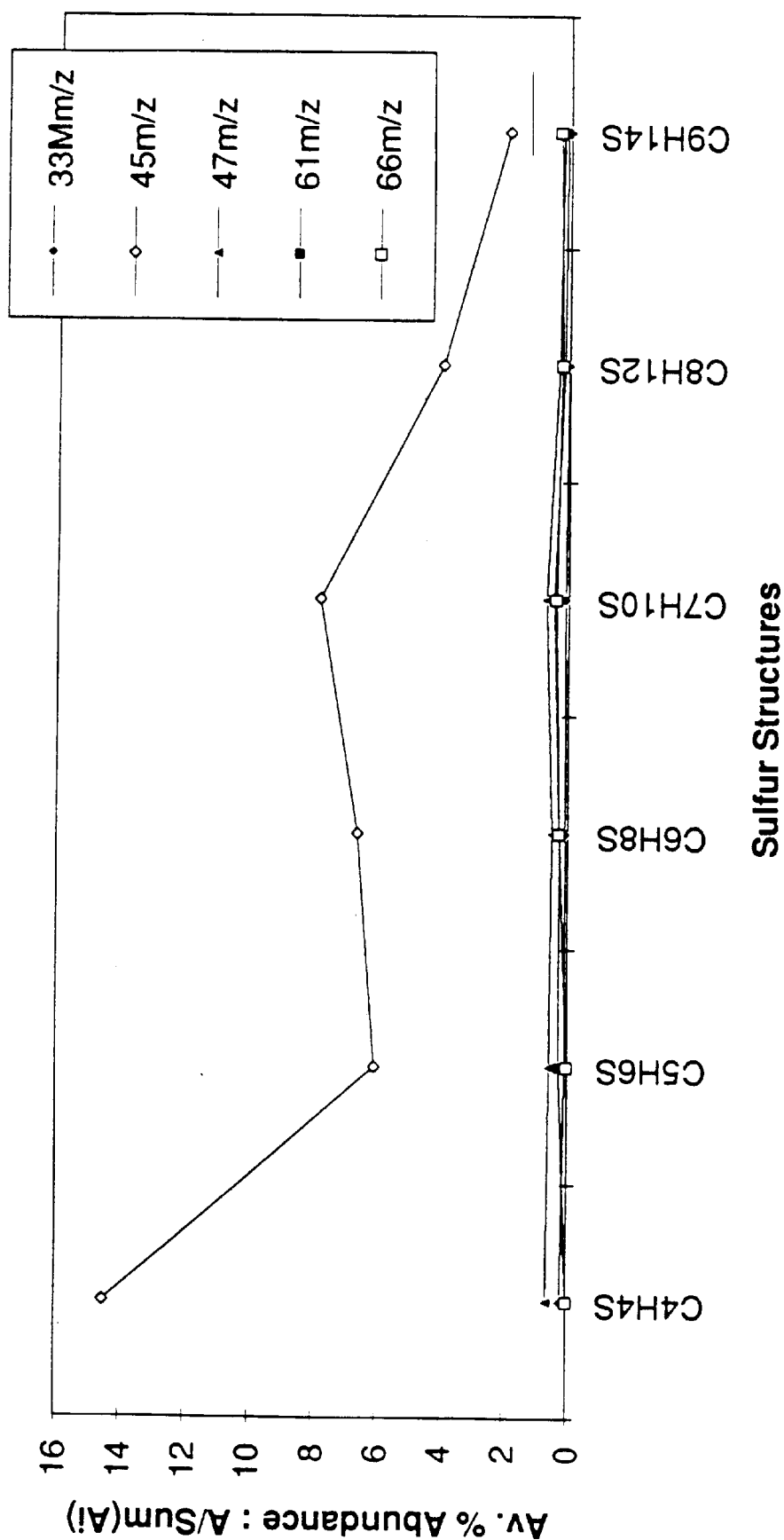
FIG. 4 is a graph showing the relative abundances of selected mass ions in the mass spectra of thiophenes.

For any given parent species, the relative abundance of each of the fragment ions over the total ionization of the particular compound making up the parent species was discovered to be different depending on the type of parent species. The results are shown in FIGS. 2–4 which show the average relative abundances of selected fragment ions for homologous members of RSR, RSH (FIG. 2), RSSR (FIG. 3) and thiophenes (FIG. 4). The hydrocarbyl sulfides and mercaptans have been grouped together based on their chemical similarity. The fragment ion with mass/charge 33 is weak in all types of spectra. The fragment ion at m/z 61 is intense in the spectra of RSR/RSH. The fragment ion at m/z 45 is intense in the spectra of thiophenes. Excluding the first spectra in RSR/RSH series ($C_2H_6S$), the ion m/z 47 is present in both RSR/RSH and RSSR spectra in approximately the same ratio, and is very weak in the spectra of the thiophenes. The ion m/z 66 is more intense in the spectra of RSSR.

As a first approximation, the ion $CHS^+$ (m/z 44.9799) can be used to measure the total sulfur content in a sample. This approximation has been made previously by Gallegos, Anal. Chem., 1975, 45, 1150 to monitor all sulfur compounds in fluid catalytic cracker heavy naphtha. However, this approximation includes both aromatic and non-aromatic sulfur-containing species. Ions $C_2H_5S^+$ (m/s 61.0112) and $H_2S_2^+$ (m/z 65.9598) can be used to monitor the amount of RSR/RSH and RSSR, respectively. The ion $CH_3S^+$ is very weak in thiophenes, and since it is approximately in the same ratio in both RSR/RSH and RSSR, it can be used to quantitatively monitor the TRS content in a sample. Thus $CH_3S^+$ (m/z 47) is the preferred fragment ion for quantitatively determining TRS.

As can be seen from FIGS. 2–4, the relative abundances of ions with m/z 45, 61 and 66 change with the different homologs in a series. In addition, both RSR/RSH and RSSR produce m/z 61 and 66 and cannot be used exclusively for each type. Therefore, there is a certain error in the evaluation of the sulfur amount when assuming a direct relationship between the measured mass spectral area and the actual sulfur quantity. Nevertheless, the methodology can be used on a relative basis, when comparing samples of similar origin with different sulfur types.

The actual limitation in using the above noted characteristic fragment ions to determine low concentrations of various reactive sulfur types is the working resolution attainable by the mass spectrometer. The resolution requirements for separation of ions $CHS^+$, $CH_3S^+$, $C_2H_5S^+$ and $H_2S_2^+$ vary widely based on the permutations of C, H, N and O. If all four of C, H, N and O are present, very high resolution (90,000) would be required. In practice, most of the possible elemental compositions are either very weak or are not present in typical petroleum samples. Thus an average resolution of 10,000 is adequate to separate most ions. Attaining higher resolution requires a sacrifice in sensitivity.

Low voltage electron ionization primarily forms molecular ions, and the resolution required for separation of higher molecular weight structures necessitates higher resolution settings according the equation: Resolution=m/$\Delta$m where m is the ion mass and $\Delta$m is the difference between the mass of the ion and the mass of the nearest interfering ion.

The precise method of measuring TRS in a given sample may vary according to the type of mass spectrometer (MS) available. A tandem MS/MS instrument can be used to directly measure TRS with maximum sensitivity. High resolution (HR) 70 eV electron ionization can be used for the relative monitoring of the various sulfur types in crude oils and refinery streams. HR can attain more accurate results by using the response factors for each compound type. The concentrations of various sulfur types are obtained by HR measurement of ion abundances and a calibration matrix determined from known sulfur mixtures according to conventional methods. HR can be coupled with a gas chromatograph to correlate TRS with boiling points for a given sample. Low resolution (LR) 70 eV electron ionization can predict the concentration of sulfur species based on multiple linear regression analysis of samples with known concentrations of sulfur types. This method is the most practical for field measurements where more complex MS instruments are not available. Mass spectral data may be acquired in the selected ion monitoring (SIM) mode.

GC/MS utilizes a gas chromatograph interfaced with a mass spectrometer. While any chromatographic method may be used to separate the mixture into components, capillary gas chromatography is the preferred means for interfacing with a mass spectrometer. The sample to be analyzed is first injected into a GC where the sample components are separated as a function of retention time and boiling point. Only partial chromatographic resolution of sample components is necessary. Components may also be identified by a detector such as a flame ionization detector, thermal conductivity detector, atomic emission detector or electron capture detector. The separated or partially separated components are then transferred to the mass spectrometer by a heated capillary line interface. In this manner, a series of mass spectra can be obtained which are correlated with retention times and hence boiling point distribution of the sample under investigation. This provides a correlation of TRS species as a function of boiling point.

When using the low resolution (LR) MS method for determining TRS, one cannot normally directly monitor the exact mass of the characteristic fragment ion in the presence of interfering hydrocarbon species. As this method only measures the nominal mass of an ion, it is coupled with a multiple linear regression calibration to obtain TRS values. In order to distinguish between the signal of the mass spectra of the ion of interest and signal due to interferences, a representative set of known samples is subjected to LR MS analysis, and the contribution of desired and interfering components is mathematically determined. Due to the complexity of typical samples, it is not feasible to prepare standard calibration mixtures that would adequately represent the many different sulfur compounds in petroleum.

While there are many mathematical tools for handling the data generated by the known samples, a preferred method is based on a multiple linear regression approach. In multiple linear regression, a series of equations is created by measuring the ion abundances $A_{ij}$ of a number of representative samples I with known TRS concentrations $C_i$. The equations are as follows:

$$C_1 = b + a_1 A_{11} + a_2 A_{12} + a_3 A_{13} + \ldots + a_j A_{1i}$$
$$C_2 = b + a_1 A_{21} + a_2 A_{22} + a_3 A_{23} + \ldots + a_j A_{2i}$$
$$C_3 = b + a_1 A_{31} + a_2 A_{32} + a_3 A_{33} + \ldots + a_j A_{3i}$$
$$\vdots$$
$$C_i = b + a_1 A_{i1} + a_2 A_{i2} + a_3 A_{i3} + \ldots + a_j A_{ij}$$

Solutions of the above equations produces the coefficients b and $a_j$. The TRS concentration for an unknown sample is determined from the measured ion abundances and the known coefficients. Although for the solution of the system one needs i=j, generally the condition i>j is allowed in order to account for the presence of the same TRS concentration is samples with different hydrocarbon chemical compositions. A better analysis includes the ion abundances of the contributing interfering hydrocarbons. Although a typical LR MS spectrum using a quadrupole MS can acquire ions with up to 800 Dalton masses, for reasons of simplicity, the preferred approach is restricted to the minimum number of possible characteristic TRS ions. Monitoring a smaller set of selected ions also increases considerably the detection limit of the instrument because more time is spent in signal accumulation and less in scanning between peaks. Based on analysis of a comparison of many known samples with standard wet chemical analysis vs LR MS, the LR MS method measures TRS within the repeatability of wet chemical method with at least a 95% confidence.

The methods of the invention are further illustrated by the following examples.

EXAMPLE 1

The instrumental procedures are described in this example. Mass spectra were obtained using a JEOL JMS-AX505WA double focusing MS. This instrument contains an electrostatic sector (E) and a magnetic analyzer (B) in a forward geometry arrangement (Electric Field/Magnetic Field). The JEOL MS instrument is based on a virtual image double focusing ion optics design with a 1:4 image magnification. For a given resolution setting, the main slit width is four times wider than the collector slid width. The overall effect is to allow the entrance of a wider ion beam into the analyzer and thus increase the maximum sensitivity.

Samples were introduced into the MS through a heated inlet system, a Hewlett-Packard 5890 gas chromatograph or a dynamic batch type inlet system. The dynamic batch system allows the direct introduction of the sample in a manner analogous to the sample introduction in a GC injection port using a carrier gas. The advantages of this system are the short time required for analysis and the capabilities of automation using an autosampler for the routine analysis of samples.

High resolution experiments were performed at 7,500 resolution. Collision induced dissociation (CID) was done using helium as a collision gas. The pressure in the collision cell, located in the first field-free region, was set to achieve a 50% attenuation of the main beam. MS/MS spectra were obtained using linked scans at constant B/E (daughter ion scan) and at constant $B^2$ (1-E)/$E^2$ (neutral loss).

EXAMPLE 2

This example is directed to the direct measurement of TRS using MS/MS. CID spectra of various sulfur fragments were obtained at constant B/E scan using the instrument described in Example 1. This scan mode allows the acquisition of the daughter ions produced upon collisional dissociation of the selected parent ion structure. The B/E CID spectra of the ion $CH_3S^+$ at m/z 47 are shown in Table 1 for the designated sulfur compounds: 1=2-methylthiophene; 2=2,3-dimethylthiophene; 3=2,5-dimethylthiophene; 4=ethyldisulfide; 5=isopropyldisulfide; 6=n-propyldisulfide; 7=benzothiophene; 8=n-butyldisulfide and 9=dibenzothiophene.

TABLE 1

| m/z | 1 | 2 | 3 | 4 | 5 | 6 | 7 | 8 | 9 |
|-----|---|---|---|---|---|---|---|---|---|
| 15 | 0.2 | 1.6 | 0.3 | 0.1 | 1.2 | 0.5 | 0 | 0.3 | |
| 25 | 1.3 | | 1.0 | 0.1 | 0.9 | | 2.6 | 0.1 | |
| 26 | 1.3 | 0.4 | 0.6 | 1.0 | 1.9 | 0.8 | 0.9 | 0.3 | 5.2 |
| 27 | | 0.3 | 0.9 | 0.4 | 1.7 | 1.0 | 1.1 | 0.3 | |
| 28 | 0.6 | 0.1 | | 0.5 | 0.2 | 0.4 | 1.0 | 0.1 | 1.0 |
| 29 | | 0.1 | 0.1 | 1.5 | 0.1 | | 0.3 | 0.5 | 2.7 |
| 30 | | | 0.6 | | | | 0.2 | | 1.1 |
| 31 | 0.3 | | 0.1 | | | | 1.0 | | |
| 32 | 4.2 | 6.1 | 4.5 | 4.7 | 2.9 | 2. | 10.8 | 1.5 | 10.4 |
| 33 | 1.2 | 4.0 | 1.8 | 2.9 | 2.9 | 2.1 | 2.1 | 2.1 | 3.9 |
| 34 | 1.7 | 1.0 | 2.7 | 1.7 | 0.6 | 0.8 | 4.9 | 0.6 | |
| 35 | | | 1.4 | 0.8 | | | 2.8 | 0.1 | 2.9 |
| 36 | 0.6 | | | 0.2 | 0.3 | | 5.2 | 0.1 | 11.9 |
| 37 | 2.9 | 0.1 | 2.2 | 0.3 | 0.6 | 0.3 | 6.4 | 0.4 | 18.0 |
| 38 | 2.3 | | 2.4 | 0.1 | 0.8 | 0.2 | 5.1 | 0.3 | 18.7 |
| 39 | 2.1 | 0.3 | 3.3 | 0.2 | 1.9 | 0.8 | 9.8 | 0.7 | |
| 40 | 1.4 | 0.4 | 0.8 | | 0.5 | 0.3 | 1.3 | 0.3 | 1.5 |
| 41 | 0.4 | 1.2 | 2.2 | 0.7 | 2.1 | 0.8 | 0.6 | 1.0 | 2.8 |
| 42 | | 0.2 | 0.1 | | 0.1 | 0.19 | | 0.2 | |
| 43 | 0.1 | | 0.1 | | 5.1 | 2.14 | 1.0 | | |
| 44 | 24 | 7.9 | 4.4 | 4.0 | 5.1 | 4.14 | 3.4 | 3.2 | 12.4 |
| 45 | 11.5 | 39.1 | 14.2 | 13.3 | 16.7 | 15.35 | 11.2 | 14.3 | 13.2 |
| 46 | 7.8 | 11.5 | 9.8 | 7.1 | 3.4 | 4.32 | 13.5 | 4.5 | 16.8 |
| 47 | 100 | 100 | 100 | 100 | 100 | 100 | 100 | 100 | 100 |

As can be seen from Table 1, an intense transition is observed at m/z 45 ($CHS^+$). Although this fragment is formed by all sulfur types when analyzed pure, the relative abundance of the parent ion m/z 47 is very weak in the spectra of thiophenes. Thus m/z 47 can be used as a TRS diagnostic. Other characterristic MS/MS transitions are as follows:

| | | | | |
|---|---|---|---|---|
| (1) | $CH_3S^+$ | → $CHS^+$ | TRS | (loss of $H_2$) |
| | 47 m/z | 45 m/z | | |
| (2) | $C_2H_5S^+$ | → $CHS^+$ | RSR/RSH | (loss of $CH_4$) |
| | 61 m/z | 45 m/z | | |
| (3) | $H_2S_2^+$ | →$S_2^+$ | RSSR | (loss of $H_2$) |
| | 66 m/z | 64 m/z | | |

The RSR/RSH and RSSR transitions are bound by the relative abundance of each parent ion in the mixture and cannot therefore be used to directly monitor the amount of the corresponding sulfur type.

Figure 5:
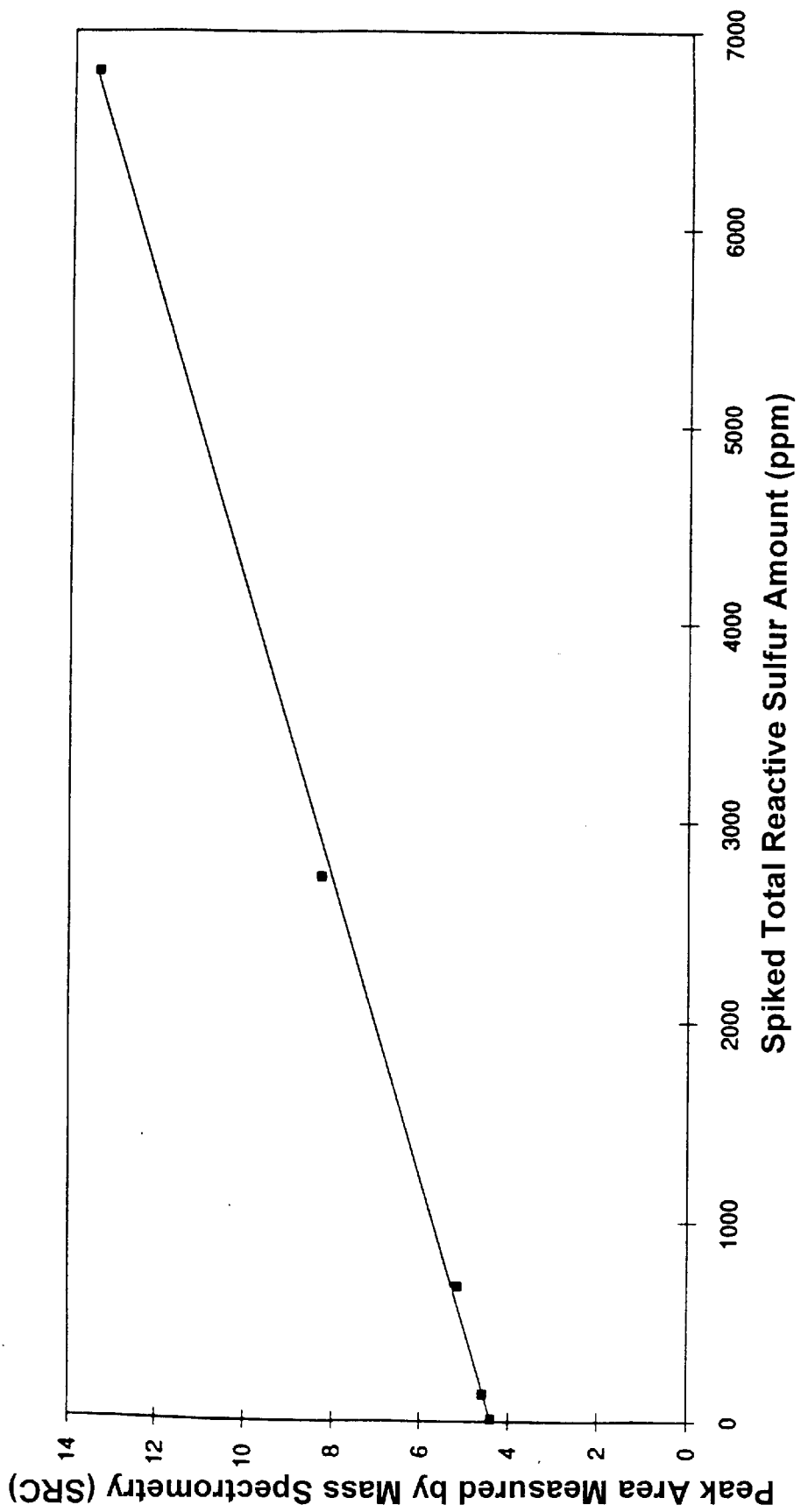
FIG. 5 is a graph showing a total reactive sulfur external calibration curve using a Nigerian medium crude spiked with known amounts of reactive sulfur compounds.

FIG. 5 shows an external calibration curve for TRS (standard addition). A Nigerian medium crude was spiked with varying amounts of a standard mixture of reactive sulfur compounds. The peak area measured with the MS is plotted against the known TRS concentration in the sample. The slope of the line represents the average TRS response factor. The intercept is a measure of the initial TRS amount in the crude. This calibration curve is for the determination of the TRS concentrations in an unknown sample.

Figure 6:
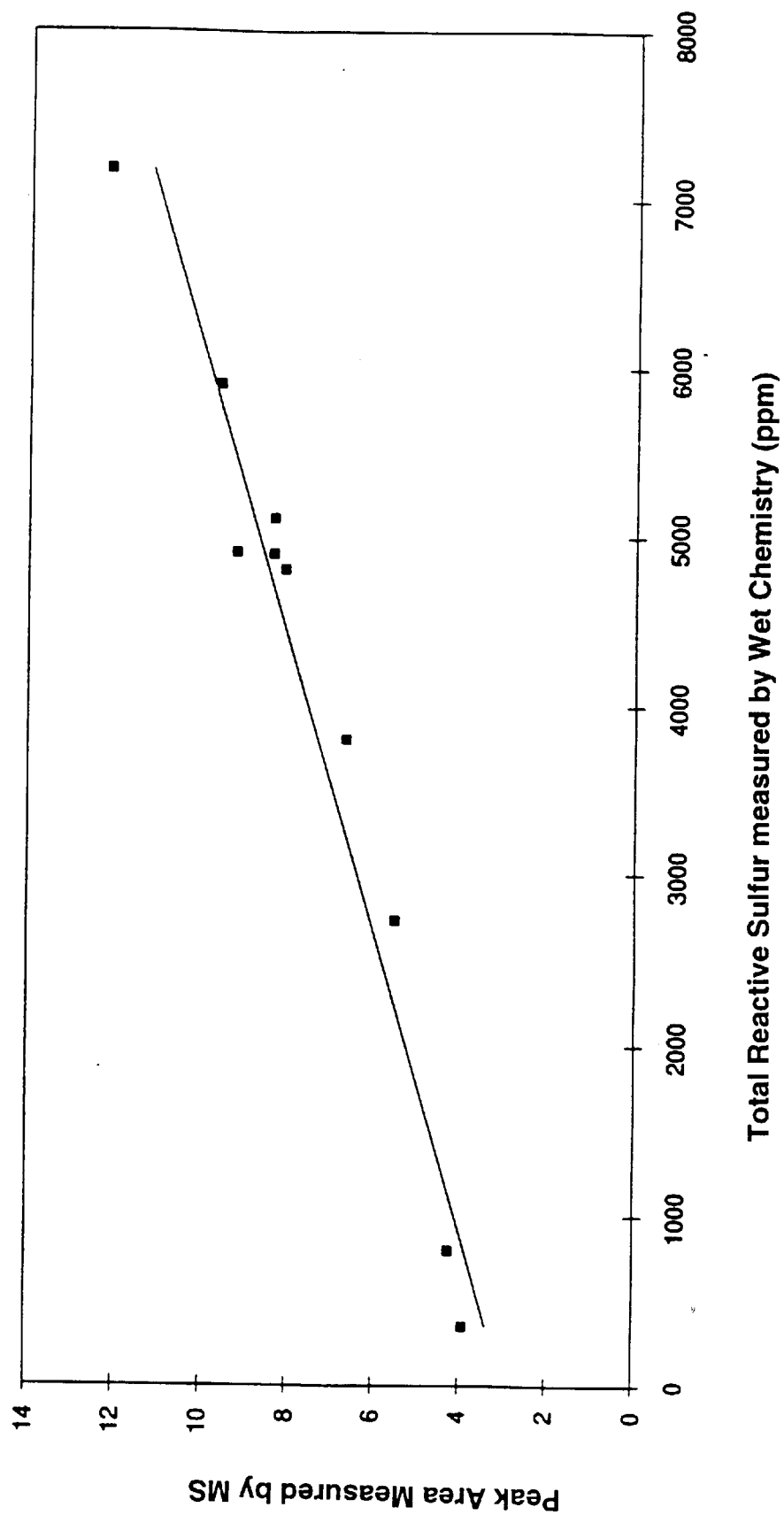
FIG. 6 is a graph showing a comparison of mass spectral areas and total reactive sulfur measured by standard wet chemical methods.

FIG. 6 shows a comparison of MS vs. wet chemical methods. The results of the comparison for a variety of crudes (New Grade, Nigerian, Murban and Cold Lake) and heavy petroleum cuts (heavy and light gas oils and reduced crudes) indicate that there is a very good (at least 95%) correlation between the two methods.

EXAMPLE 3

Figure 7:
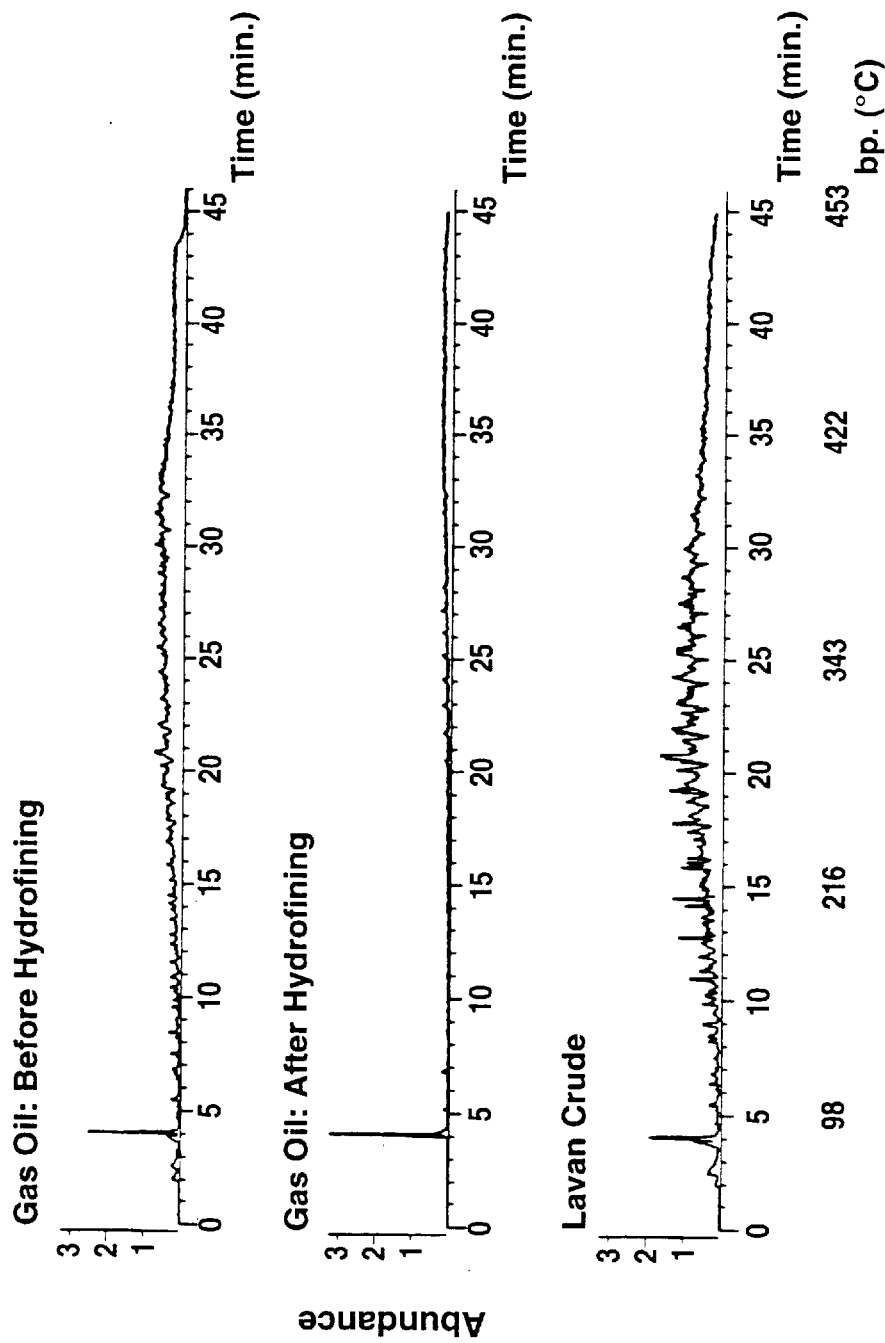
FIG. 7 is a graph showing total reactive sulfur as a function of time/boiling point for three petroleum samples.
Figure 8:
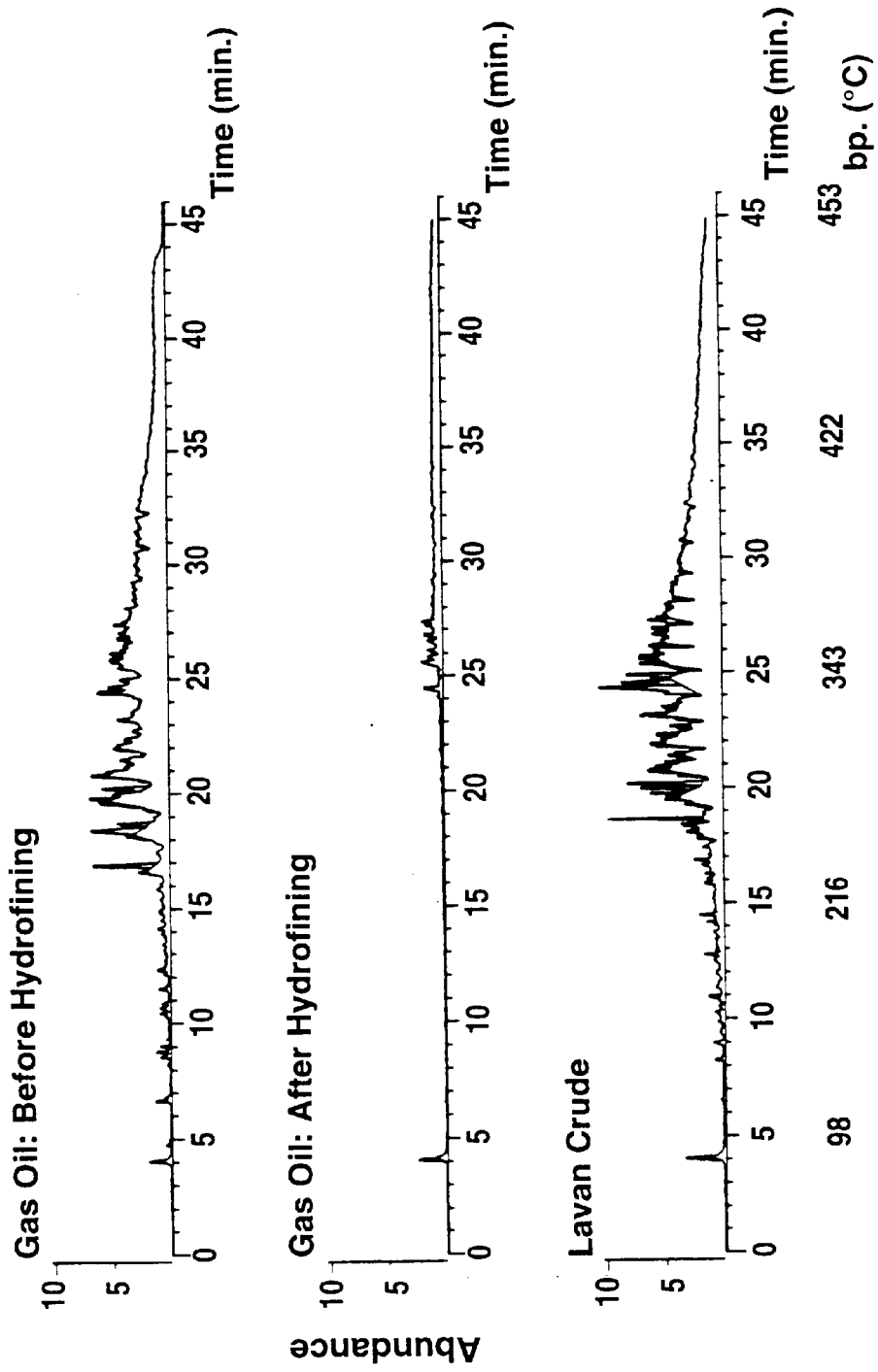
FIG. 8 is a graph showing total sulfur as a function of time/boiling point for three petroleum samples.

The use of high resolution MS to monitor TRS is shown in this Example. A kerosene was subjected to high resolution MS in the selected ion monitoring (SIM) mode. While the SIM can be used to study any of the characteristic fragment ions noted above, of particular interest is the CH3S+ ion in view of its correlation with TRS. The results for three different samples boiling in the kerosene range are shown in FIG. 7 and 8. FIG. 7 is a graph of TRS as a function of time for the three samples. FIG. 8 is a graph of total sulfur as a function of time.

EXAMPLE 4

Figure 9:
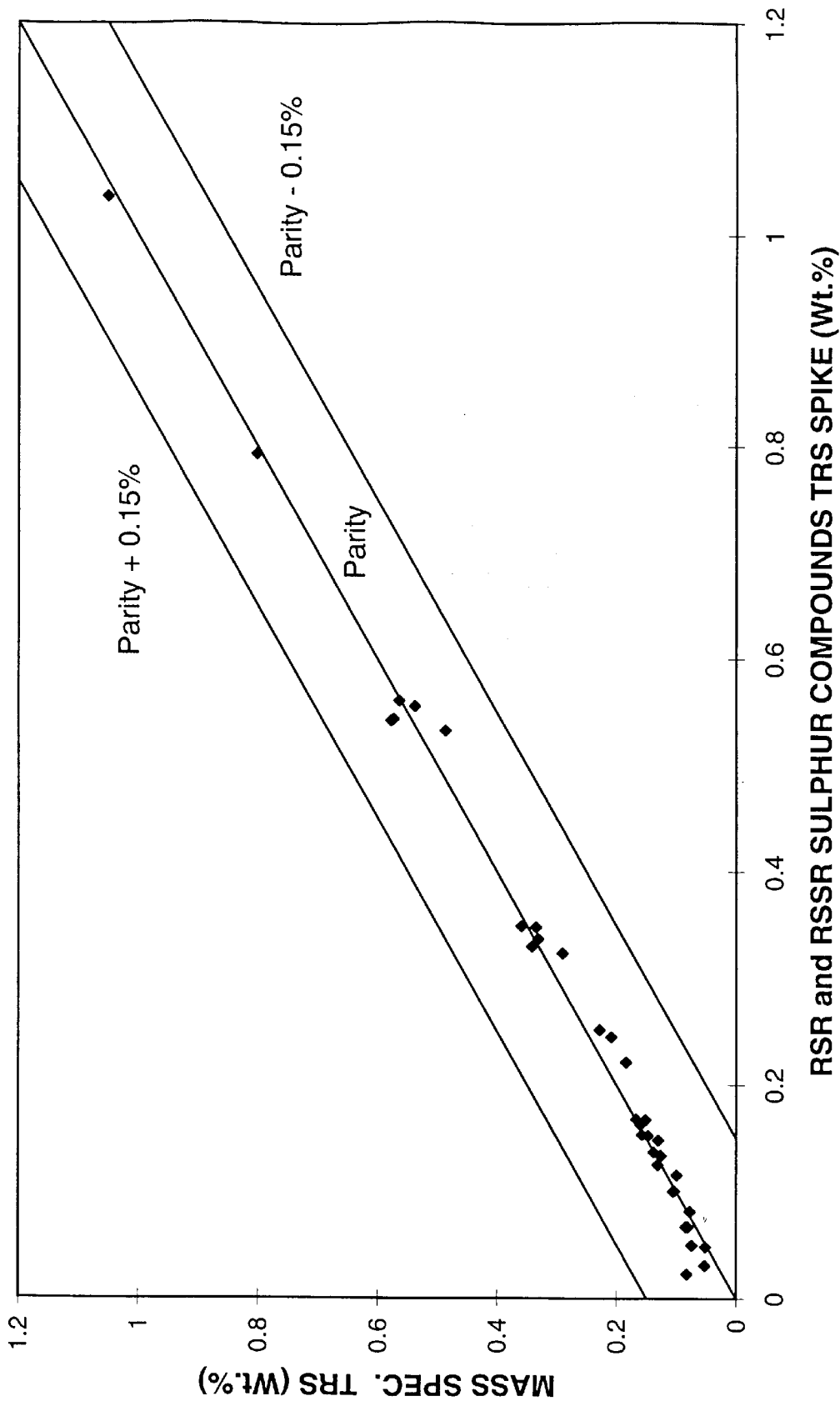
FIG. 9 is a graph showing a calibration chart of total reactive sulfur using model sulfur compounds.

This example is directed to the use of low resolution (LR) MS for the determination of TRS. A Brunfeldt batch type system was used for the introduction of sample into a Hewlett-Packard 5970 mass spectrometer. Samples were introduced either through an ampoule which was heated under vacuum or in the case of light samples, through a gallium frit inlet. The spectrometer was calibrated using perfluorobutylamine. Data were obtained by scanning the desired range (33–80 Daltons) or in the SIM mode. A series of MS for crudes spiked with different concentrations of standard sulfur mixtures were obtained and the appropriate coefficients from a multiple linear regression analysis of the data were obtained. The calibration equation is $$[TRS\text{-}Wt.\%] = 0.1591 + 0.1100 A_{45} + 1.2596 A_{47} - 0.0116 A_{51} - 0.0568 A_{61} - 0.0006 A_{64} - 0.0644 A_{66}$$

with an average absolute error between the known and measured TRS values of 0.0163S-wt.%. The coefficient of correlation is 0.9908. The calibration chart is shown in FIG. 9 which is a graph of TRS using model sulfur compounds. Whole crudes, distillate and resid cuts are spiked with RSR and RSSR compounds.

Figure 10:
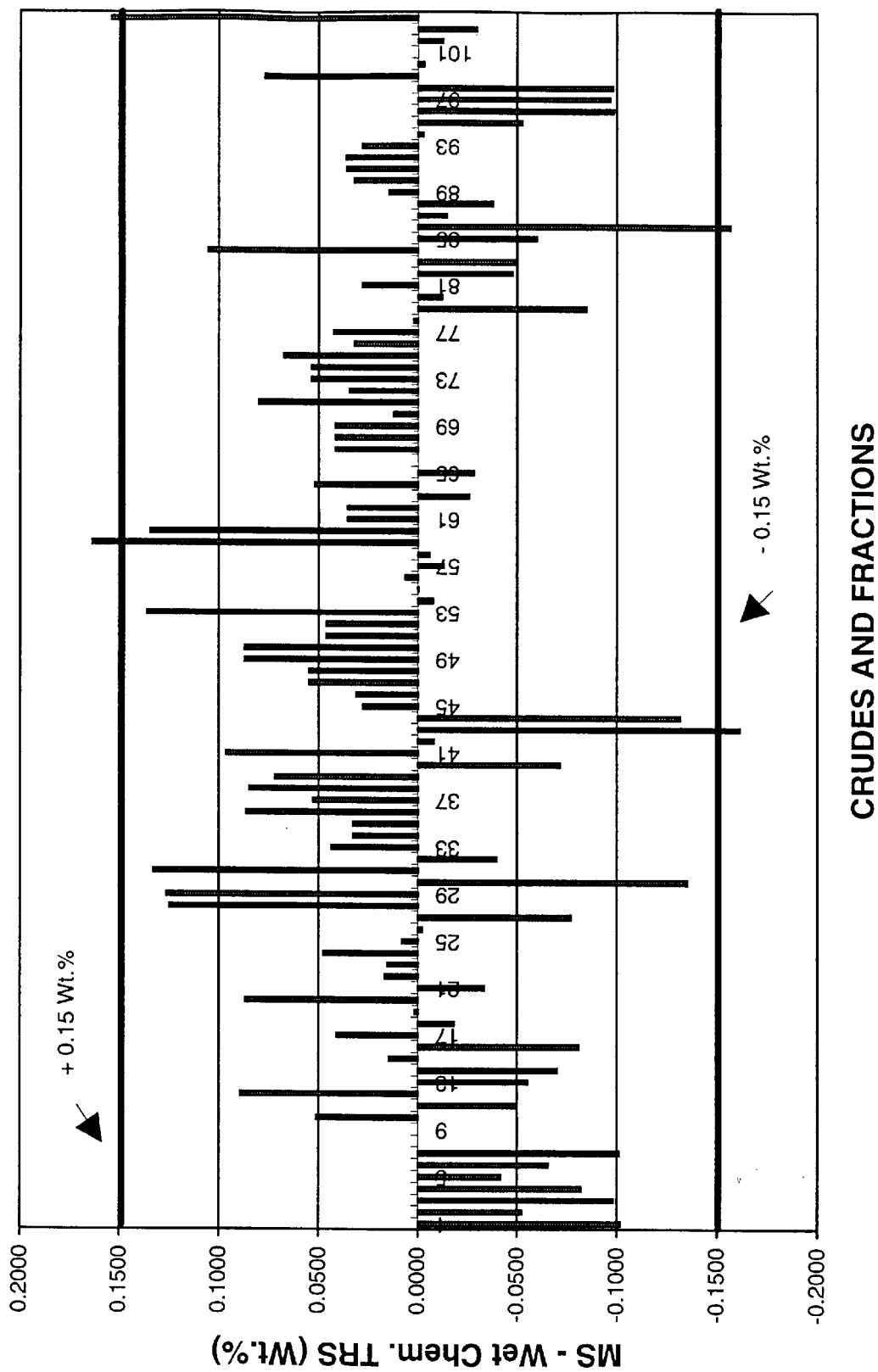
FIG. 10 is a graph showing a validation chart for the mass spectrometry total reactive sulfur method.

A series of over 100 samples varying from whole crudes of differing character to distillate cuts were analyzed using standard wet chemical techniques and TRS determined from LR MS. The average absolute difference of the results obtained with the LR MS method as compared to the wet chemical method is 0.056%. FIG. 10 is a graph of the TRS difference measured by MS from the wet method for these samples. The average difference from FIG. 10 is 0.0083 wt.%. This demonstrates that there is virtually no bias between LR MS and wet methods over a large set of data.

The LR MS method has the advantages that it is simple, rapid, precise and accurate and is amenable to refinery and field operations where expensive MS equipment is not available. Crudes with specific gravities between 0.75 and 1.10, and total sulfur values up to 7.0 S-wt.% have been successfully analyzed using this technique. The method is applicable to even wider ranges of crudes and fractions thereof.

What is claimed is:

1. A method of determining total reactive sulfur as a function of boiling point for a crude oil or fraction thereof which comprises the steps of:
    (1) introducing the crude oil or fraction thereof containing aromatic and non-aromatic sulfur compounds into a chromatographic separation means which is interfaced to a mass spectrometer thereby causing at least a partial separation of the crude oil or fraction thereof into constituent chemical components as a function of retention time;

(2) introducing the constituent chemical components into a mass spectrometer;

(3) obtaining a series of time resolved mass spectra;

(4) selecting fragment ions which are characteristic of non-aromatic reactive sulfur species including hydrogen sulfide, mercaptans, hydrocarbyl sulfides, hydrocarbyl disulfides, elemental sulfur and polysulfides, said fragment ions being selected from at least one of the group consisting of $SH^+$, $CHS^+$, $CH_3S^+$, $C_2H_5S^+$, $H_2S_2^+$, and $S_2^+$;

(5) identifying peaks in the mass chromatogram which are characteristic of at least one of the fragment ions; and (6) quantifying the reactive sulfur species identified by their corresponding fragment ions as a function of retention time, wherein the total reactive sulfur is the weighted sum of the individual non-aromatic reactive sulfur species.

2. The method of claim 1 wherein the fragment ion is selected from $CSH^+$, $CH_3S^+$, $C_2H_5S^+$ and $H_2S_2^+$.

3. The method of claim 1 wherein the fragment ion is $CH_3S^+$.

4. The method of claim 1 wherein the chromatographic separation means is a gas chromatograph.

5. The method of claim 4 wherein the gas chromatograph is a capillary gas chromatograph.

* * * * *